US009433444B2

(12) United States Patent
Humphreys et al.

(10) Patent No.: US 9,433,444 B2
(45) Date of Patent: *Sep. 6, 2016

(54) SURGICAL INSTRUMENT SYSTEM AND METHOD

(71) Applicant: Warsaw Orthopedic, Inc., Warsaw, IN (US)

(72) Inventors: Kevin R. Humphreys, Memphis, TN (US); Marc T. Paul, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 130 days.

This patent is subject to a terminal disclaimer.

(21) Appl. No.: 14/161,951

(22) Filed: Jan. 23, 2014

(65) Prior Publication Data

US 2015/0201976 A1      Jul. 23, 2015

(51) Int. Cl.
*A61B 17/70* (2006.01)
*A61B 17/17* (2006.01)

(52) U.S. Cl.
CPC ....... *A61B 17/7074* (2013.01); *A61B 17/1728* (2013.01); *A61B 17/1757* (2013.01)

(58) Field of Classification Search
CPC .......... A61B 17/7074; A61B 17/7076; A61B 17/7059
USPC ....... 606/280, 281, 289, 295, 99, 104, 86 A, 606/86 B
See application file for complete search history.

(56) References Cited

U.S. PATENT DOCUMENTS

| 5,423,826 | A * | 6/1995 | Coates et al. | 606/96 |
| 6,746,454 | B2 * | 6/2004 | Winterbottom et al. | 606/99 |
| 7,166,111 | B2 * | 1/2007 | Kolb et al. | 606/96 |
| 7,468,064 | B2 * | 12/2008 | Bruneau et al. | 606/99 |
| 2004/0204717 | A1 * | 10/2004 | Fanger et al. | 606/96 |

* cited by examiner

*Primary Examiner* — Pedro Philogene
*Assistant Examiner* — David C Comstock

(57) ABSTRACT

A surgical guide comprises a member including an inner surface defining at least one cavity configured for disposal of at least one surgical tool and at least one part movable relative to the member and including a lock element engageable with a lock element of a spinal implant. Systems and methods are disclosed.

20 Claims, 8 Drawing Sheets

SURGICAL INSTRUMENT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, implants such as bone fasteners, plates, connectors and vertebral rods are often used to provide stability to a treated region. These implants can redirect stresses away from a damaged or defective region while healing takes place to restore proper alignment and generally support the vertebral members. For example, plates may be attached via the fasteners to the exterior of one or more vertebral members. This disclosure describes an improvement over these prior art technologies.

SUMMARY

In one embodiment, a surgical guide is provided. The surgical guide comprises a member including an inner surface defining at least one cavity configured for disposal of at least one surgical tool and at least one part movable relative to the member and including a lock element engageable with a lock element of a spinal implant. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

Figure 1:
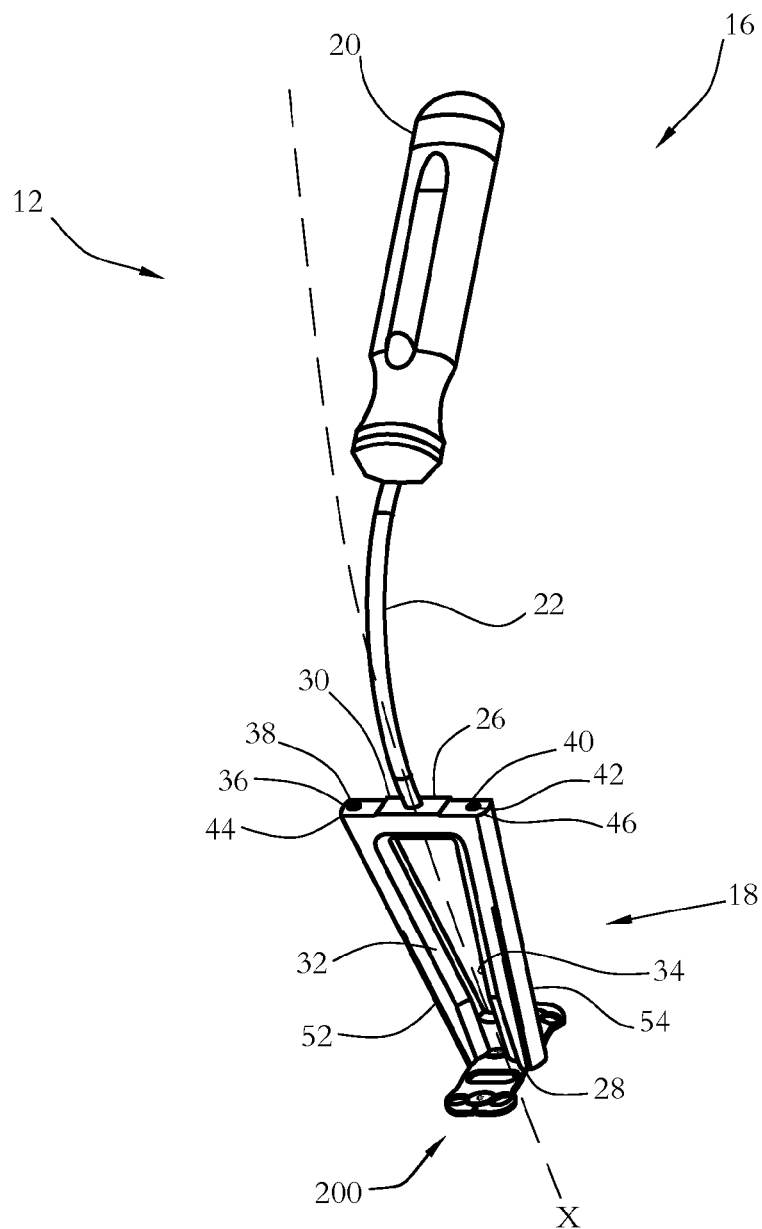
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine.

In one embodiment, the present system includes a surgical instrument, such as, for example, a drill, tap and screw (DTS) guide, which can be employed with a plating system for attachment and/or docking. In one embodiment, the surgical instrument can be employed with a low profile plating system for various orthopedic applications. In one embodiment, the surgical instrument can be employed with a low profile plating system including a plate having a wall thickness of approximately 1 millimeter (mm) of usable docking surface. In one embodiment, the surgical instrument is engageable with a plate in a mating pin and slot configuration. In one embodiment, the pin and slot are disposed in a parallel orientation. This configuration optimizes the docking surface for a secure connection at a fixed angle.

In one embodiment, the pin and slot mating configuration is employed for securing the surgical instrument to a spinal plate. In one embodiment, the surgical instrument allows for docking and removal with a single hand. In one embodiment, the pin and slots secure a spinal plate, allowing the practitioner to dock at a fixed angle. In one embodiment, the DTS guide is docked and a practitioner can drill, tap or place a screw down shafts of the DTS guide.

In one embodiment, the system of the present disclosure includes an implant support having a locking mechanism for a surgical guide. In one embodiment, the lock ensures that the engagement of the surgical guide to the implant support is not compromised under normal use.

In one embodiment, the pin and slot mating configuration include an interface that allows the DTS guide to flex during docking and/or removal. In one embodiment, the surgical instrument includes arms, each arm having an inside face including a rod and/or mating pin that engages mating slots on an outside surface of a plate. In one embodiment, the present system includes a surgical instrument for holding, drilling, tapping and screwing without moving the surgical instrument and with limited invasiveness.

In one embodiment, one or all of the components of the surgical system are disposable, peel-pack, pre-packed sterile devices used with an implant. One or all of the components of the surgical system may be reusable. The surgical system may be configured as a kit with multiple sized and configured components. In one embodiment, the surgical system includes one or a plurality of guides, each guide be configured for disposal with a plate at a different angle.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-8, there are illustrated components of a surgical system 10, including a surgical instrument, such as, for example, a surgical guide 12 in accordance with the principles of the present disclosure.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

The components of surgical system 10 including surgical guide 12 are employed, for example, with a minimally invasive procedure, including percutaneous techniques, mini-open and open surgical techniques to deliver and introduce an implant, such as, for example, one or a plurality of bone fasteners and/or spinal plates, at a surgical site within a body of a patient, for example, a section of a spine. In some embodiments, surgical guide 12 delivers and introduces a spinal plate for fixation with an anterior side of a spine. In some embodiments, surgical guide 12 is configured to facilitate drilling and/or tapping of tissue, such as, for example, vertebrae, and/or guiding, fastening and/or driving fasteners, such as, for example, bone screws with the vertebrae using one or a plurality of surgical tools, which tools may be alternately disposed with surgical guide 12 during a procedure.

Surgical guide 12 is configured for connecting to a plate 200, as discussed herein. Surgical guide 12 extends along a longitudinal axis x between a portion, such as, for example, a handle 16 and a portion, such as, for example, a member 18. As shown in FIG. 1, an intermediate portion, such as, for example a shaft 22 is disposed between handle 16 and member 18.

Member 18 extends between an end 26 and an end 28. Member 18 includes an extension 32 and an extension 34. Extension 32 extends between ends 26, 28. In some embodiments, the width of extension 32 may be constant between end 26 and end 28. In some embodiments the width of extension 32 may be uniformly increasing or decreasing between end 26 and end 28. Extension 32 includes an inner surface 36 that defines an inner cavity, such as, for example, a passageway 38. In some embodiments, passageway 38 is tubular with a cylindrical cross-sectional configuration. In some embodiments, passageway 38 may have alternate cross-sectional configurations, such as, for example, oval, oblong, triangular, rectangular, square, polygonal, irregular, uniform, non-uniform, variable and/or tapered.

Extension 34 extends between ends 26, 28. In some embodiments, the width of extension 34 may be constant between end 26 and end 28. In some embodiments the width of extension 34 may be uniformly increasing or decreasing between end 26 and end 28. Extension 34 includes an inner surface 40 that defines an inner cavity, such as, for example, a passageway 42. In some embodiments, passageway 42 is tubular with a cylindrical cross-sectional configuration. In some embodiments, passageway 42 may have alternate cross-sectional configurations, such as, for example, oval, oblong, triangular, rectangular, square, polygonal, irregular, uniform, non-uniform, variable and/or tapered.

Figure 2:
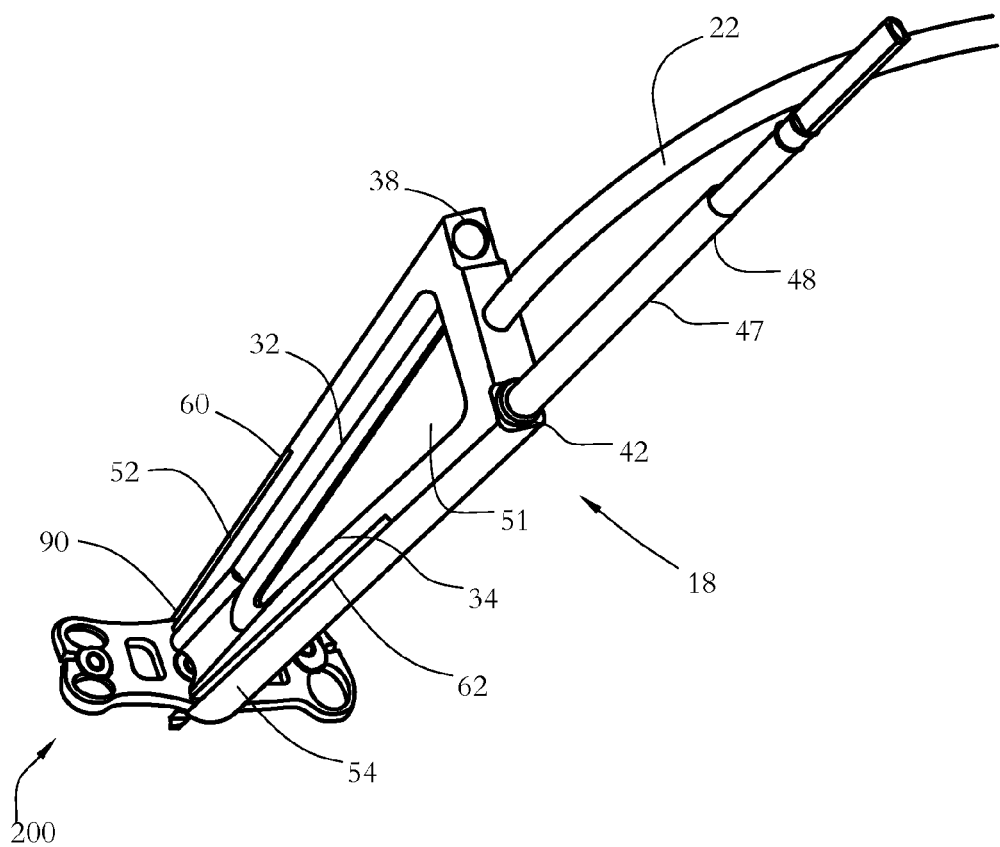
FIG. 2 is a break away perspective view of components of one embodiment of a surgical system in accordance with the principles of the present disclosure.
Figure 3:
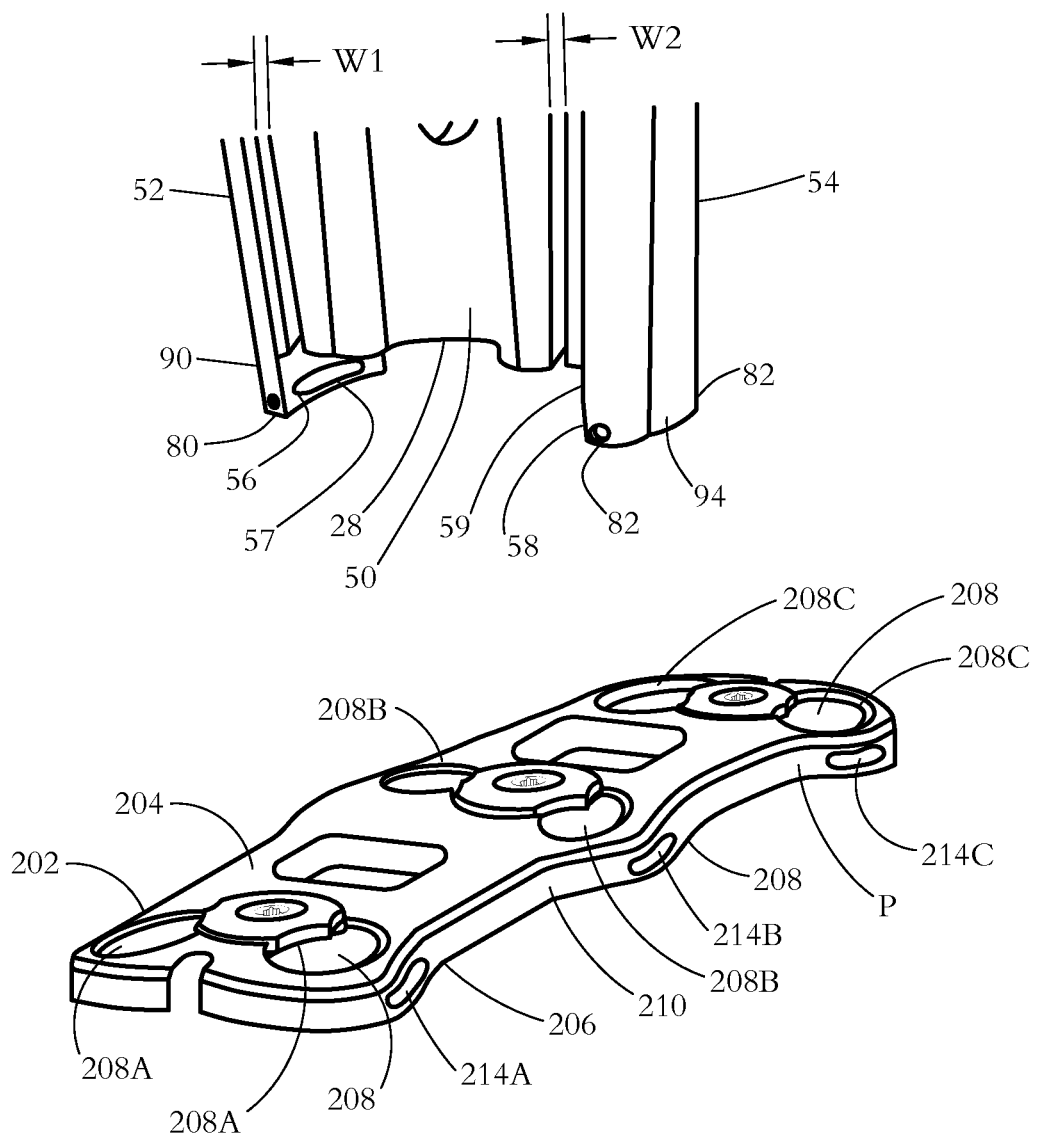
FIG. 3 is a break away perspective view of the components shown in FIG. 1.

Extension 32 and extension 34 are spaced apart and separated along longitudinal axis x, forming an opening 51, as shown in FIG. 2. In some embodiments, extension 32 and extension 34 may be connected or attached at an intermediate portion, such as, for example, junction 50, as shown in FIG. 3, adjacent end 28. In some embodiments, opening 51 may have alternate cross-sectional configurations, such as, for example, oval, oblong, triangular, rectangular, square, polygonal, irregular, uniform, non-uniform, variable and/or tapered to facilitate pivoting.

In some embodiments, surfaces 36, 40 include a layer of friction-reducing material (not shown). In some embodiments, the layer may include an insert and/or a coating comprising silicone, poly(tetrafluororthene), lubricants and/or material examples, as described herein. In some embodiments, the layer of friction-reducing material provides an even interface between surfaces 36, 40 and an outer surface 47 of a surgical tool, such as, for example, a drill 48, as shown in FIG. 2. In some embodiments, all or only a portion of inner surfaces 36, 40 may have alternate surface configurations, such as, for example, planar, rough, undulating, porous, semi-porous, dimpled, polished and/or textured.

End 26 includes an end surface 30. End surface 30 includes an opening 44 and an opening 46. Opening 44 is in communication with passageway 38. Opening 46 is in communication with passageway 42. Passageways 38, 42 extend axially from openings 44, 46, respectively. In some embodiments, passageways 38, 42 extend from openings 44, 46 in alternate configurations such as, for example, offset and/or staggered. In other embodiments, passageways 38, 42 may extend at transverse orientations from openings 44, 46, relative to longitudinal axis x, such as, for example, perpendicular and/or other angular orientations such as acute or obtuse, co-axial and/or parallel.

Passageways 38, 42 are configured for movable disposal of a surgical tool, for example, drill 48. Passageways 38, 42 are configured for disposal of surgical instruments to deliver one or more implants to a surgical site, as will be described. In some embodiments, the surgical tool may comprise one or a plurality of tools, such as, for example a drill, a tap, and/or a driver that may be alternately disposed with passageway 38 and/or passageway 42. In one embodiment, passageways 38, 42 may be configured to guide the surgical tool into alignment with plate 200, a fastener and/or tissue.

Figure 6:
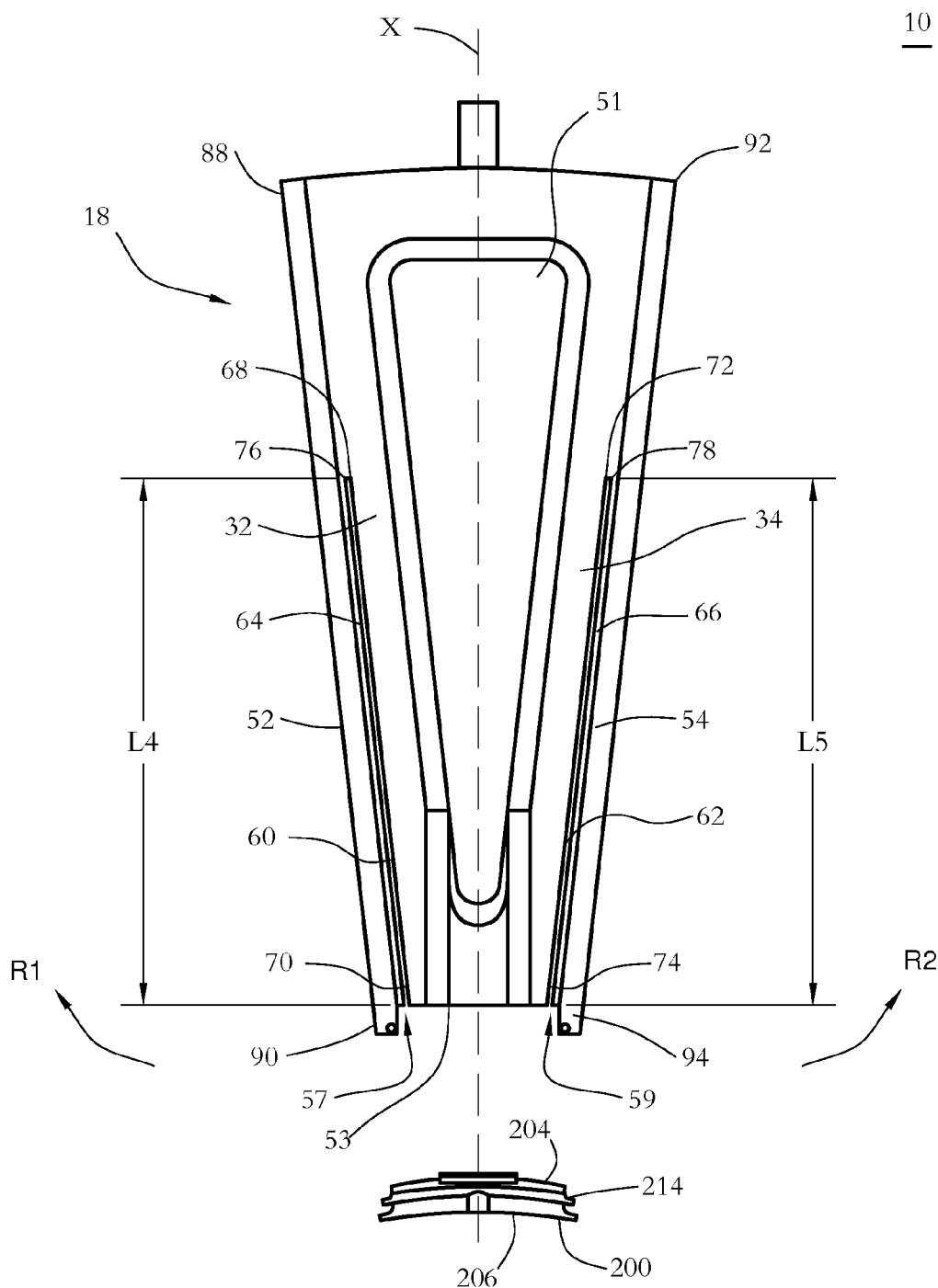
FIG. 6 is a break away side view of the components shown in FIG. 1.

Member 18 includes a part, such as, for example, an arm 52 disposed adjacent extension 32 and a part, such as, for example, an arm 54 disposed adjacent extension 34. Arm 52 extends along longitudinal axis x between an end 88 and an end 90, as shown in FIG. 6. Arm 52 includes an inner surface 64. In some embodiments, surface 64 communicates with passageway 38.

Figure 4:
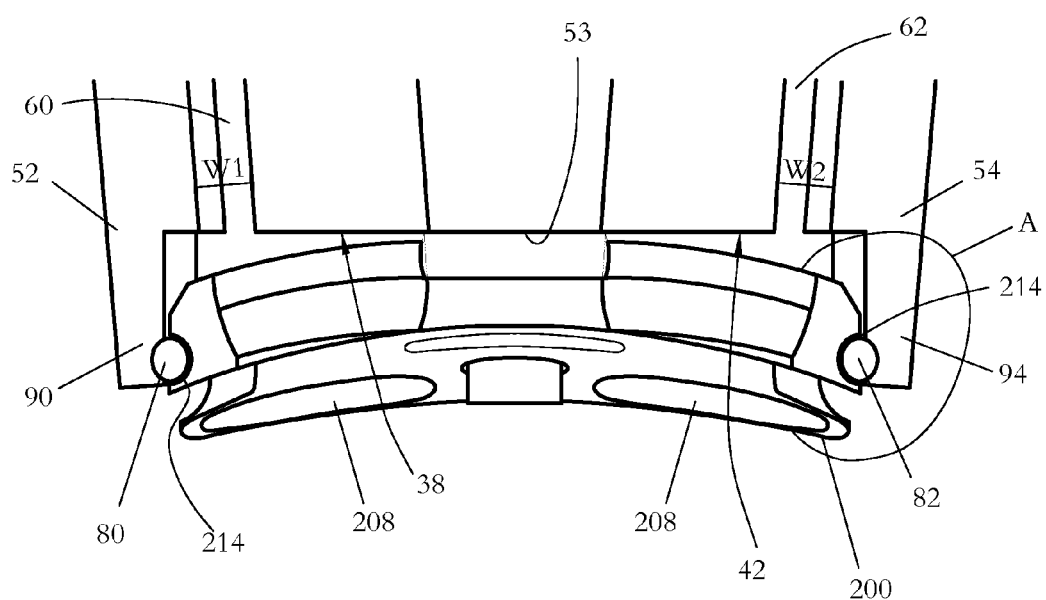
FIG. 4 is a break away, side cross section view of the components shown in FIG. 1.
Figure 5:
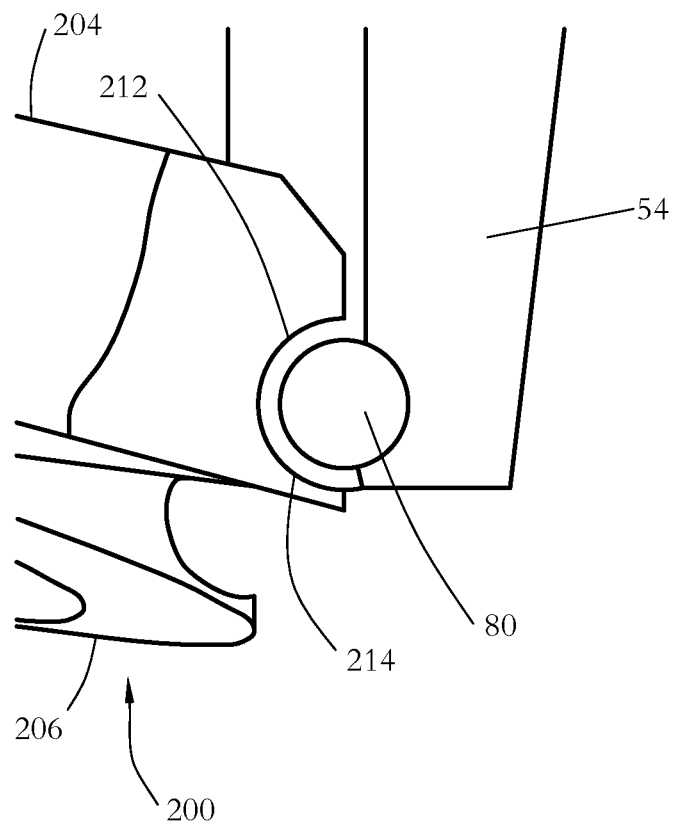
FIG. 5 is an enlarged view of detail A shown in FIG. 4.

As shown in FIG. 3, end 90 extends a distance beyond end 28 of member 18. End 90 includes an inner surface 56 that defines a cavity 57. A lock element, such as, for example, a pin 80, as shown in FIGS. 3-5, is disposed with cavity 57 for capture of plate 200, as described herein. Pin 80 is configured for mating and releasable engagement with a lock element, such as, for example, a surface of a slot of plate 200, as discussed herein. In one embodiment, the lock element may include mating elements such as, for example, clips, hooks, adhesives, spring loaded buttons and/or flanges.

Arm 54 is disposed adjacent an opposite side of junction 50. Arm 54 extends along longitudinal axis x between an end 92 and an end 94. Arm 54 includes an inner surface 66. In some embodiments, surface 66 communicates with passageway 42. Junction 50 includes a surface 53 configured to engage a surface of plate 200, as described herein, to prevent disengagement of the locking elements of guide 12 and plate 200. In some embodiments, surface 53 is a mating surface configured to control a vertical position of member 18 relative to a lock element of plate 200. As shown in FIG. 4, surface 53 is engageable with and contacts plate 200. Surface 53 is disposed in a parallel orientation relative to slots 214, described herein, of plate 200. In some embodiments, surface 53 may have alternate surface configurations, such as, for example, planar, rough, undulating, dimpled, polished and/or textured to facilitate engagement with plate 200. In some embodiments, this configuration prevents disengagement of arms 52, 54 from plate 200 due to the downward force provided for engagement of arms 52, 54 with the locking elements of plate 200, for example, engagement of surface 53 with a surface of plate 200 prevents arms 52, 54 from overextending beyond plate 200.

End 94 extends a distance beyond end 28 of member 18. End 94 includes an inner surface 58 that defines a cavity 59. A lock element, such as, for example, a pin 82 is disposed with cavity 59 for capture of plate 200, as described herein. Pin 82 is configured for mating and releasable engagement with a surface of a slot of plate 200, as discussed herein.

Member 18 includes an elongate opening, such as, for example, a slot 60 defined between arm 52 and extension 32, as shown in FIG. 6. Slot 60 is configured to provide a freedom of movement, which includes rotation and/or pivoting of arm 52 relative to extension 32 for capture of plate 200. Slot 60 extends longitudinally a distance L4 along extension 32 between an end 68 and an end 70. In some embodiments, end 68 is adjacent end 26 of member 18. In some embodiments, end 70 is adjacent end 28 of member 18. In one embodiment, slot 60 may extend in alternate configurations such as, for example, having a radius of curvature, offset and/or staggered, perpendicular and/or other angular orientations such as acute or obtuse, co-axial and/or parallel. In one embodiment, slot 60 includes a width w1 along its distance L4, as shown in FIGS. 2 and 4. In some embodiments, width w1 may be uniformly increasing or decreasing, or have alternate widths along L4.

Member 18 includes an elongate opening, such as, for example, a slot 62 defined between arm 54 and extension 34, as shown in FIG. 6. Slot 62 extends longitudinally a distance L5 along extension 34 between an end 72 and an end 74. In some embodiments, distance L4 may be equal distance to L5. In some embodiments, distance L4 and distance L5 may vary in length. In one embodiment, slot 62 includes a width w2 along its distance L5, as shown in FIGS. 2 and 5. In one embodiment, width w2 may be uniformly increasing or decreasing, or have alternate widths along L5.

In some embodiments, arms 52, 54 are configured for a monolithic connection to a portion of extensions 32, 34 and flex in a pivotally movable configuration relative to extensions 32, 34. Arm 52 rotates about a pivot point 76 adjacent end 68 of slot 60, in the direction shown by arrow R1 in FIG. 6. Arm 54 rotates about a pivot point 78 adjacent end 72 of slot 62, in the direction shown by arrow R2 in FIG. 6. In some embodiments, arms 52, 54 extend in a cantilever configuration from member 18. In some embodiments, the material of member 18 adjacent pivot points 76, 78 and/or arms 52, 54 is, such as, for example, a pliable, flexible, spring-like material and/or a material configured to retain its configuration, such as, for example, Nitinol. In some embodiments, arms 52, 54 are inwardly biased to a contracted orientation such that widths w1, w2 are uniform along slots 60, 62.

In one embodiment, as arm 52 rotates relative to member 18, width w1 uniformly increases such that width w1 is greater adjacent end 70 than adjacent end 68. In one embodiment, as arm 54 rotates relative to member 18, width w2 uniformly increases such that width w2 is greater adjacent end 74 than adjacent end 72.

As shown in FIG. 3, surgical system 10 includes an implant, such as, for example, a plate 200. Plate 200 includes a stratum 202 having a surface 204 and a surface 206. Surface 206 is configured to engage tissue, such as, for example, an anterior portion of vertebrae. Stratum 202 defines a series of openings 208 extending between surface 204 and surface 206. Openings 208 are configured for disposal of permanent implantable fixation elements, such as, for example, bone screws for attaching plate 200 with tissue. Plate 200 includes three pairs of openings 208a, 208b and 208c. Stratum 202 defines an edge 210 disposed around the entire periphery P of plate 200.

Edge 210 includes surface 212 defining recesses, such as, for example, slots 214. Plate 200 includes slots 214 on opposite sides of edge 210 disposed on opposite sides of a pair of openings 208. As shown in FIG. 3, three pairs of slots 214a, 214b and 214c are disposed along edge 210. In some embodiments, surface 212 may have alternate surface configurations, such as, for example, rough, threaded for connection with surgical instruments, arcuate, undulating, porous, semi-porous, dimpled, polished and/or textured. In some embodiments, plate 200 may have various cross-sectional configurations, such as, for example, oval, oblong, triangular, square, polygonal, irregular, uniform, non-uniform, variable and/or tapered.

Figure 7:
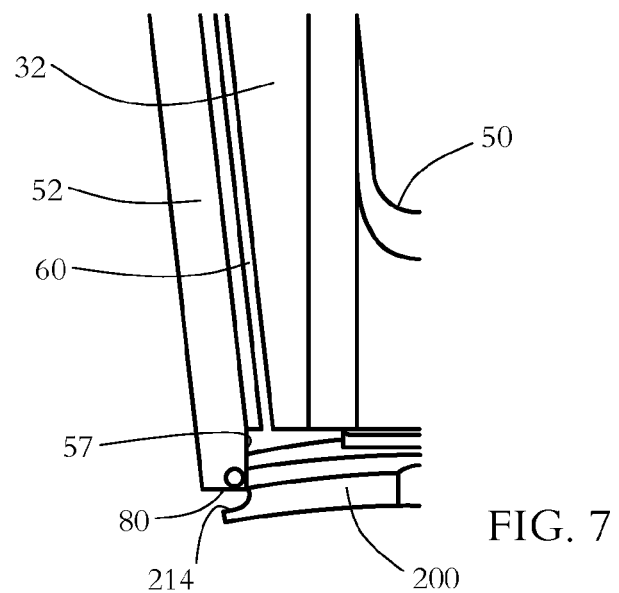
FIG. 7 is a break away side view of the components shown in FIG. 1.
Figure 8:
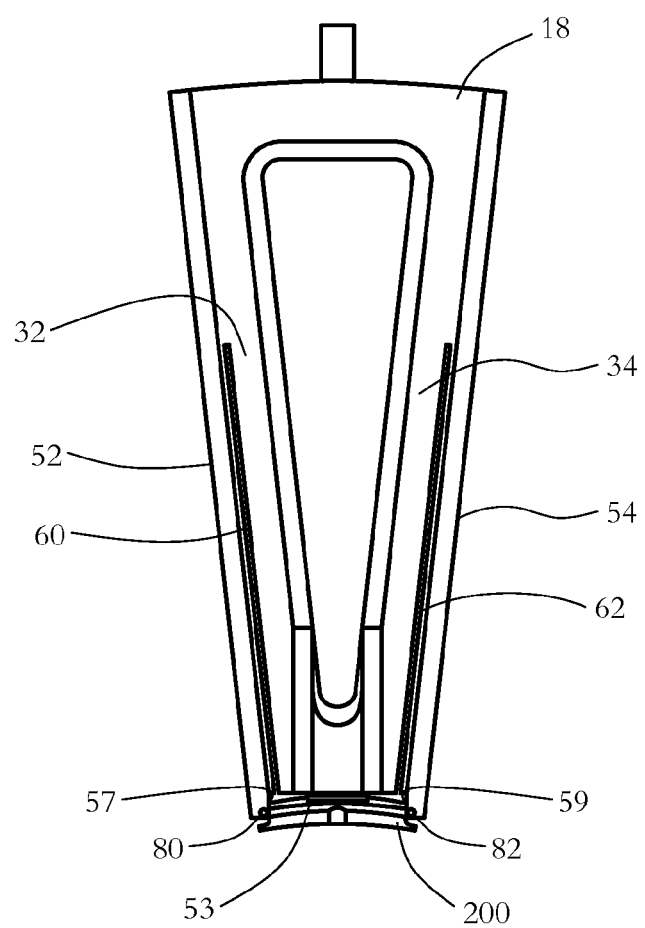
FIG. 8 is a break away side view of the components shown in FIG. 1.

Pins 80, 82 are configured to matingly engage slots 214 on opposite sides of edge 210 to releasably secure surgical guide 12 with plate 200 for insertion into a surgical site. In one embodiment, the cross-section configuration of slots 214 may correspond to the cross-sectional configuration of pins 80, 82. For example, as shown in FIGS. 4, 5 and 7, pins 80, 82 have a cylindrical configuration and slots 214 have a corresponding cylindrical configuration. In some embodiments, pins 80, 82 and/or slots 214 may have alternate cross-section configurations, such as, for example, oval, oblong, triangular, rectangular, square, polygonal, irregular, uniform, non-uniform, variable and/or tapered.

Pins 80, 82 engage edge 210 such that arms 52, 54 are caused to flex outwardly to overcome the resilient bias of arms 52, 54 to receive plate 200. Arms 52, 54 pivot about pivot points 76, 78 and arms 52, 54 expand, in the direction shown by arrows R1, R2. As pins 80, 82 are engaged with slots 214, pins 80, 82 matingly engage surface 212 of slots 214, as shown in FIGS. 4, 5 and 7. The resilient bias of arms 52, 54 cause pins 80, 82 to matingly engage inner surface 212 of slots 214 in a pressure or friction fit such that arms 52, 54 capture plate 200 in a releasable engagement and locked position. In the locked position, arms 52, 54 engage plate 200 with member 18 to prevent translation of plate 200 and resist disengagement of plate 200 from surgical guide 12.

As shown in FIG. 1, surgical guide 12 includes handle 16. Handle 16 includes a surface, such as, for example, a gripping surface 20 configured to facilitate maneuvering of surgical guide 12. In some embodiments, handle 16 is substantially cylindrical. In some embodiments, handle 16 may have various cross-sectional configurations, such as, for example, oval, oblong, triangular, rectangular, square, polygonal, irregular, uniform, non-uniform, variable and/or tapered. In some embodiments, all or only a portion of a gripping surface 20 may have alternate surface configurations, such as, for example, rough, threaded for connection with surgical instruments, arcuate, undulating, porous, semi-porous, dimpled, polished and/or textured according to facilitate gripping.

Surgical guide 12 includes an intermediate portion, such as, for example, shaft 22 disposed between handle 16 and member 18. In one embodiment, shaft 22 has a flexible configuration, which includes movement in a lateral or side to side direction. In some embodiments, all or only a portion of shaft 22 may have a semi-rigid, rigid, flexible or elastic configuration, and/or have elastic and/or flexible properties such as the elastic and/or flexible properties corresponding to the material examples described above such that shaft 22 provides a selective amount of expansion and/or extension in an axial direction. In some embodiments, shaft 22 may be compressible in an axial direction. Shaft 22 can include a plurality of separately attachable or connectable portions or sections, such as bands or loops, or may be monolithically formed as a single continuous element. In some embodiments, shaft 22 may have various lengths.

In some embodiments, one or all of the components of surgical system 10 can be delivered or implanted as a pre-assembled device or can be assembled in situ. The components of surgical system 10 may be completely or partially revised, removed or replaced.

In assembly, operation and use, surgical system 10, similar to the systems described herein, is employed to treat a selected section of vertebrae V. A medical practitioner obtains access to a surgical site including vertebrae V in any appropriate manner, such as through incision and retraction of tissues. In some embodiments, surgical system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

Figure 9:
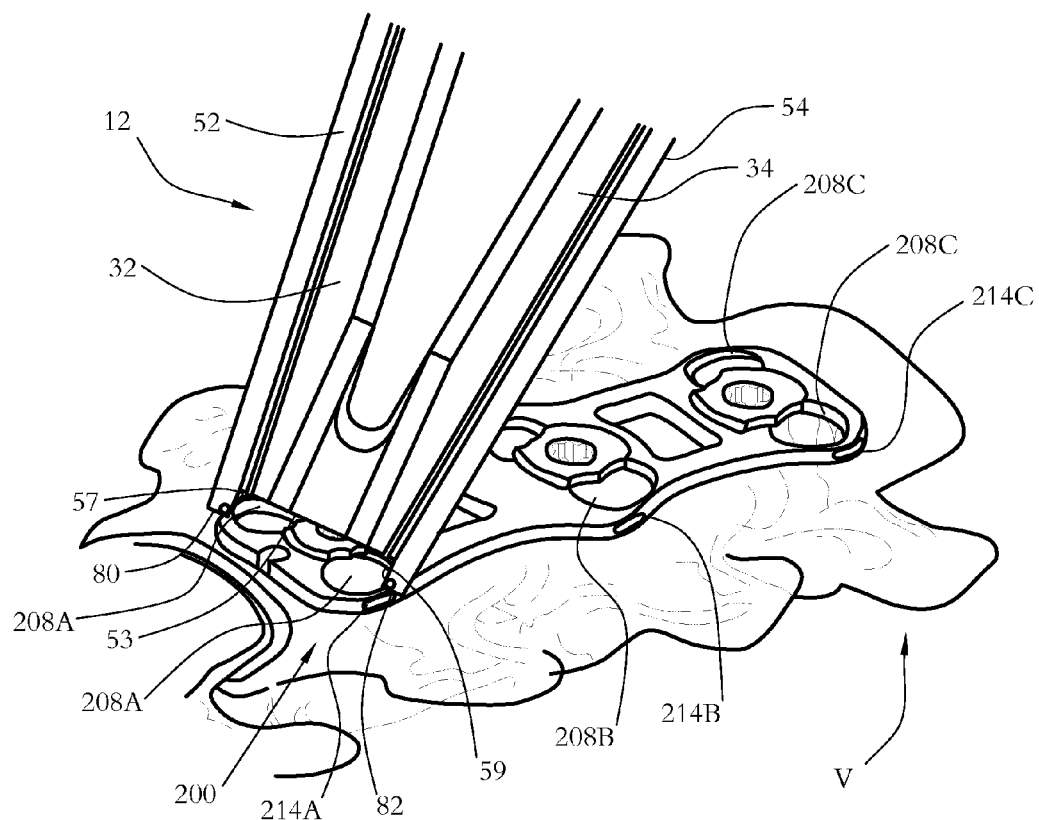
FIG. 9 is a perspective view of components of one embodiment of a surgical system in accordance with the principles of the present disclosure disposed with vertebrae.

An incision is made in the body of a patient and a cutting instrument (not shown) creates a surgical pathway for implantation of components of surgical system 10 with an anterior portion of vertebrae V, as shown in FIG. 9. A preparation instrument (not shown) can be employed to prepare tissue surfaces of vertebrae V, as well as for aspiration and irrigation of a surgical region.

Surgical system 10 includes a surgical instrument, such as, for example, a drill, tap, and screw (DTS) guide 12, as described herein. Guide 12 is connected with plate 200 and/or bone fasteners (not shown) for orientation and delivery of the components of surgical system 10 along the surgical pathway. Guide 12 introduces the components of surgical system 10 along the surgical pathway to implant plate 200 and/or bone fasteners in substantial alignment to attach plate 200 and/or bone fasteners with vertebrae V.

Guide 12 is manipulated such that pins 80, 82 engage edge 210 such that arms 52, 54 are caused to flex outwardly to overcome the resilient bias of arms 52, 54 to receive plate 200. Arms 52, 54 pivot to expand, as described herein, such that pins 80, 82 engage the surface of slots 214. Surface 53 engages the surface of plate 200 to prevent arms 52, 54 from overextending beyond plate 200 such that pins 80, 82 remain engaged with slots 214. Pins 80, 82 matingly engage surface 212 of slots 214, as shown in FIGS. 4, 5 and 7. The resilient bias of arms 52, 54 cause pins 80, 82 to matingly engage inner surface 212 of slots 214 in a pressure or friction fit such that arms 52, 54 capture plate 200 in a releasable engagement and locked position. Guide 12 delivers and introduces plate 200 for fixation with an anterior side of vertebrae V.

Guide 12 is an adaptable instrument configured to perform multiple applications during a surgical procedure. In some embodiments, guide 12 can prepare and/or create a cavity in tissue of vertebrae V. Guide 12 guides a surgical instrument, such as, for example, a drill, tap and/or an awl, as well as guiding fasteners to penetrate tissue. Surgical tools including an awl, a tap and screws are passed through guide 12. Pilot holes or the like are made in selected vertebra of vertebrae V for receiving fixation elements, such as, for example, bone screws (not shown). Plate 200 is fastened with vertebrae V via the bone screws and driver employed with guide 12.

Upon completion of the procedure, the surgical instruments, assemblies and non-implanted components of surgical system 10 are removed and the incision is closed. Surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels.

In some embodiments, surgical system 10 includes one or more fasteners, not shown, for attaching plate 200 with tissue, as described herein. In some embodiments, the fasteners may be engaged with tissue in various orientations, such as, for example, series, parallel, offset, staggered and/or alternate vertebral levels. In some embodiments, one or more of the fasteners may comprise multi-axial screw sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical guide comprising:
a member including an inner surface defining at least one cavity configured for disposal of at least one surgical tool; and
at least one part movable relative to the member and including a lock element engageable with a lock element of a spinal implant,
wherein the locking element of the at least one part includes a pin and the locking element of the spinal implant includes a slot.

2. A surgical guide as recited in claim 1, wherein the member extends between a first end including an opening communicating with the cavity and a second end.

3. A surgical guide as recited in claim 2, wherein the second end is disposed adjacent the spinal implant.

4. A surgical guide as recited in claim 1, wherein the cavity includes a passageway configured to guide the tool in alignment with the spinal implant.

5. A surgical guide as recited in claim 1, wherein the tool comprises a plurality of tools that can be alternately disposed with the cavity.

6. A surgical guide as recited in claim 1, wherein:
the member includes a first extension and a second extension spaced from the first extension, wherein the at least one cavity includes a first passageway formed in the first extension and a second passageway formed in the second extension; and
the at least one part includes a first arm and a second arm spaced from the first arm, the first arm extending beyond the first extension to capture the spinal implant and the second arm extending beyond the second extension to capture the spinal implant, the first arm being spaced apart from the first extension by a first slot and the second arm being spaced apart from the second extension by a second slot.

7. A surgical guide as recited in claim 6, wherein the arms are each monolithically connected to a portion of one of the extensions such that the arms are rotatable relative to the extensions.

8. A surgical guide as recited in claim 1, wherein the at least one part extends in a cantilever configuration from the member.

9. A surgical guide as recited in claim 1, wherein the at least one part includes a first arm and a second arm spaced from the first arm, the arms being inwardly biased.

10. A surgical guide as recited in claim 9, wherein the arms are expandable from a contracted orientation in which the arms are spaced apart a first distance to an expanded orientation in which the arms are spaced apart an increased second distance to capture the spinal implant.

11. A surgical guide as recited in claim 1, wherein the at least one part extends beyond the member to capture the spinal implant.

12. A surgical guide comprising:
- a member defining a longitudinal axis and including an inner surface defining at least one cavity configured for disposal of a plurality of tools that can be alternately disposed with the at least one cavity;
- a first arm extending from the member in alignment with the longitudinal axis, the first arm including a locking element; and
- a second arm extending from the member in alignment with the longitudinal axis, the second arm including a locking element,
- wherein the locking elements are pins and the arms are movable relative to the member such that the locking elements matingly engage slots of a spinal implant.

13. A surgical guide as recited in claim 12, wherein the arms capture the spinal implant such that the spinal implant is disposed at a selected and fixed angle relative to the longitudinal axis.

14. A spinal implant system comprising:
- a guide defining a longitudinal axis and including an inner surface defining at least one passageway, the guide further including arms movable relative thereto and being disposed in alignment with the longitudinal axis, each of the arms including a locking element disposed transverse to the longitudinal axis;
- a plate including locking elements, wherein the locking elements of the arms are expandable to engage the locking elements of the plate such that the plate is captured with the guide and disposed at a selected and fixed angle relative to the longitudinal axis; and
- a surgical tool disposable in the at least one passageway,
- wherein the locking element of the guide includes a pin and the locking elements of the plate are slots.

15. A spinal implant system as recited in claim 14, wherein the arms extend in a cantilever configuration from the guide.

16. A spinal implant system as recited in claim 14, wherein the arms are rotatable relative to the guide.

17. A spinal implant system as recited in claim 14, wherein the at least one passageway includes an opening disposed in alignment with an opening in the plate.

18. A spinal implant system as recited in claim 14, wherein the plate comprises a first surface and an opposite second surface that is configured to engage tissue of a patient, the plate comprising a plurality of spaced apart openings that each define an opening axis, the slots each extending along an axis that extends transverse to the opening axes.

19. A spinal implant system as recited in claim 18, wherein the plate comprises an edge that extends from the first surface to the second surface, the slots each extending into the edge.

20. A spinal implant system as recited in claim 14, wherein the pin is positioned in a cavity in one of the extensions.

* * * * *